United States Patent
Brooksby et al.

(10) Patent No.: US 9,091,528 B2
(45) Date of Patent: Jul. 28, 2015

(54) SYSTEM AND METHOD FOR OBJECT MEASUREMENT

(71) Applicant: GENERAL ELECTRIC COMPANY, Schenectady, NY (US)

(72) Inventors: Glen William Brooksby, Glenville, NY (US); Paulo Ricardo dos Santos Mendonca, Clifton Park, NY (US); Denisa Narmour Borges, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 203 days.

(21) Appl. No.: 13/796,521

(22) Filed: Mar. 12, 2013

(65) Prior Publication Data

US 2013/0188042 A1 Jul. 25, 2013

Related U.S. Application Data

(63) Continuation of application No. 11/020,893, filed on Dec. 23, 2004, now Pat. No. 8,396,329.

(51) Int. Cl.
| | |
|---|---|
| G06K 9/32 | (2006.01) |
| G01B 11/02 | (2006.01) |
| G01N 21/95 | (2006.01) |
| G01N 21/952 | (2006.01) |
| G06K 9/00 | (2006.01) |
| G06T 7/00 | (2006.01) |

(52) U.S. Cl.
CPC ............ *G01B 11/022* (2013.01); *G01N 21/952* (2013.01); *G01N 21/9515* (2013.01); *G06K 9/00208* (2013.01); *G06T 7/001* (2013.01); *G06T 7/0028* (2013.01)

(58) Field of Classification Search
USPC ............................... 356/401; 382/294; 700/57
See application file for complete search history.

(56) References Cited

U.S. PATENT DOCUMENTS

| | | | |
|---|---|---|---|
| 6,201,549 B1 | 3/2001 | Bronskill | |
| 6,377,371 B1 * | 4/2002 | Baba et al. ....................... | 359/23 |
| 6,639,594 B2 | 10/2003 | Zhang et al. | |
| 6,865,289 B1 * | 3/2005 | Berestov ....................... | 382/154 |
| 6,975,326 B2 | 12/2005 | Baumberg et al. | |
| 7,098,435 B2 | 8/2006 | Muller et al. | |
| 2003/0011596 A1 | 1/2003 | Zhang et al. | |
| 2003/0066949 A1 | 4/2003 | Mueller et al. | |
| 2003/0085890 A1 * | 5/2003 | Baumberg et al. ............ | 345/420 |

FOREIGN PATENT DOCUMENTS

EP 0524479 A1 * 1/1993 ............... G01B 3/02

OTHER PUBLICATIONS

K. Kim et al., "The Perspective Silhouette of a Canal Surface", Computer Graphics Forum, The Eurographics Association and Blackwell Publishing Ltd., vol. 22, No. 1, pp. 15-22, 2003.

* cited by examiner

*Primary Examiner* — Gregory F Cunningham
(74) *Attorney, Agent, or Firm* — John P. Darling

(57) ABSTRACT

A technique is provided for measuring an object based on multiple views. The technique includes registering each of the plurality of images and a first model of the object with one another and reconstructing a second model of the object based on the plurality of images and the first model registered with one another.

20 Claims, 5 Drawing Sheets

SYSTEM AND METHOD FOR OBJECT MEASUREMENT

This application is a continuation of U.S. Ser. No. 11/020,893 filed on Dec. 23, 2004.

BACKGROUND

The invention relates generally to the field of industrial metrology and, in particular, to model-based measurement techniques using multiple views.

Measurement of objects is of vital importance in manufacturing and repair industries. Various types of measurement systems, such as computed tomography (CT), coordinate measuring machines (CMM), laser-based profilometry, and infrared, are used for industrial inspection. For example, these measurement systems may be used for measuring dimensions or for identifying defects in manufactured parts, such as tubes. Unfortunately, many of these measurement systems are costly, slow to produce, bulky, application specific, and require high maintenance. For example, different gauges are often required for different tubes. Also, in many applications the tubes considered are smooth surfaces without texture or fiducial markings, and therefore current techniques that rely on point correspondences cannot be employed, as the accuracy level is lower than acceptable. As the manufacturing tolerances become tighter, there is a corresponding increase in the demands for metrology techniques for maintaining the tolerances. The need for quality and performance testing has become an integral part of the production or manufacturing process.

Accordingly, a need exists for a measurement technique that is relatively inexpensive, versatile and programmable for different applications and that requires low maintenance.

BRIEF DESCRIPTION

Briefly, in accordance with one embodiment of the technique, a method is provided for measuring an object. The method includes registering each of a plurality of images and a first model of the object with one another. The plurality of images comprises different views of the object. The method also includes reconstructing a second model of the object based on the plurality of images and the first model registered with one another. In certain embodiments, the technique may include systems and computer programs that afford such functionality.

In accordance with another embodiment of the present technique, a measurement system is provided. The measurement system includes a plurality of imaging devices for acquiring a plurality of images of at least a part of the object from a plurality of viewpoints and a modeling system coupled to the plurality of imaging devices. The modeling system is configured to register each of the plurality of images and a first model of the object with one another. The modeling system is also configured to reconstruct a second model of the object based on the plurality of images and the first model registered with one another.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the present technique are generally directed toward a method and system for model-based measurement using images of multiple views of an object/target. These measurement techniques may be useful in a variety of contexts where a complex part, such as a curved section of a tube, needs to be measured and compared against design parameters. Although the following discussion is limited to a few examples, a variety of applications are within the scope of the present technique.

Figure 1:
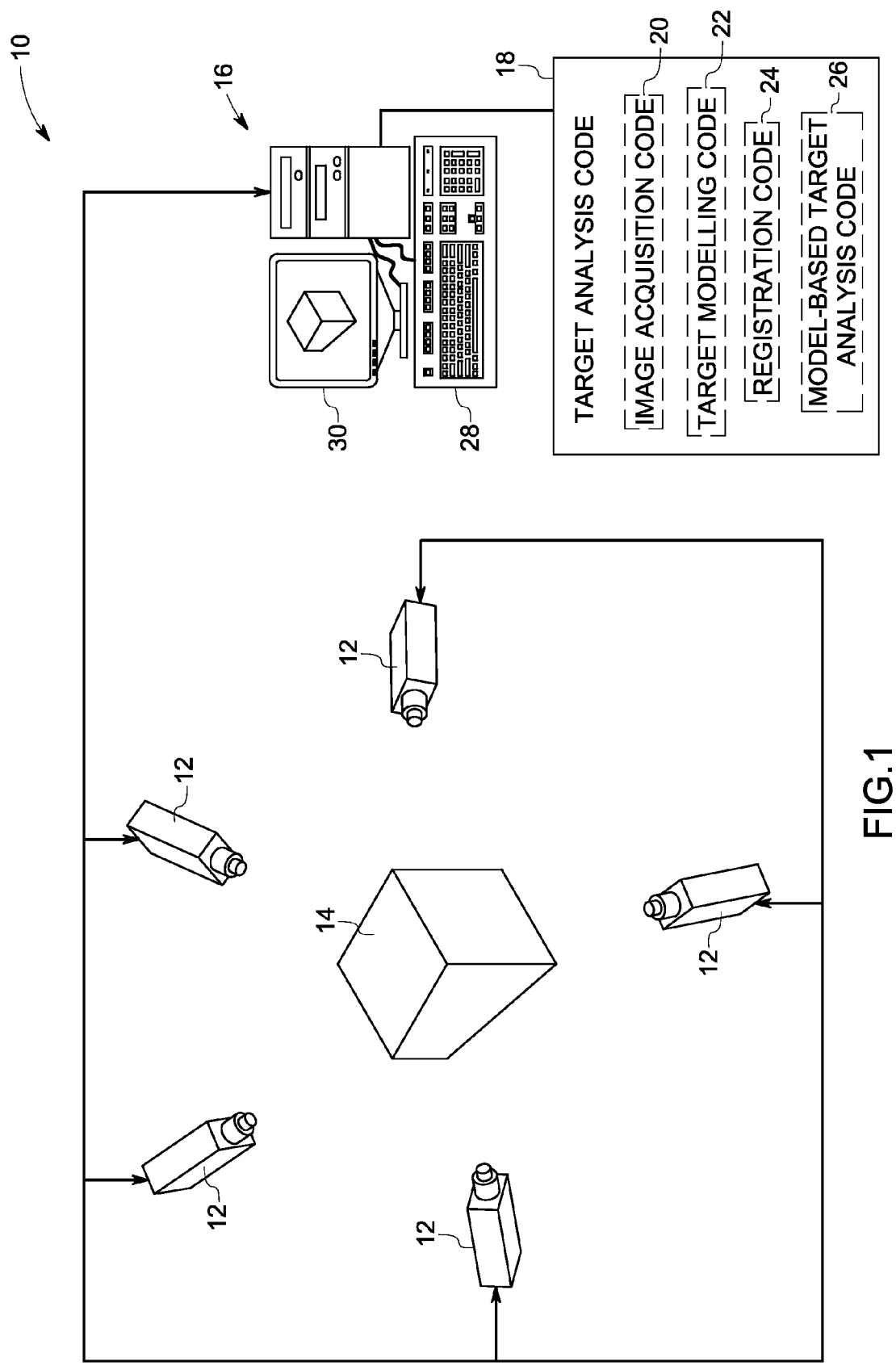
FIG. 1 is a diagrammatical illustration of an exemplary system having multiple imaging devices, a computer, and target analysis code in accordance with certain embodiments of the present technique.

Referring now to FIG. 1, this figure illustrates an exemplary measurement system 10 in accordance with the present technique. In the illustrated embodiment, the measurement system 10 may include one or more imaging devices 12 placed at various viewpoints for acquiring multiple images of an object/target 14 under inspection. In certain embodiments, the imaging devices 12 may be analog and/or digital cameras, such as still or video cameras. Alternatively, a single imaging device 12 may be employed and the imaging device 12 or object 14 may be moved with respect to the other, such that the imaging device 12 can acquire images of multiple views of the object 14. These images of different viewpoints cumulatively provide a full view of the desired span of interest or area of coverage of the object 14. As discussed in further detail below, these multiple images from different viewpoints and a first model of the object are registered with one another, and are then used to create a second model of the object 14 that may be used to obtain measurements of the object 14. It should be noted that, in certain embodiments, the first model of the object 14 may be registered with the multiple images from different viewpoints to create the second model of the object 14. Alternatively, in certain embodiments, the multiple images from different viewpoints may be registered with the first model of the object 14 to create the second model of the object 14. In other words, the registration between images and the first model may be performed by processing (e.g., transforming, warping, matching, etc.) the first model to be registered with the images, by processing each of the images to be registered with the first model, by processing the first model and each of the images to be registered with another reference or coordinate system, or by a combination of processing both the first model and one or more of the images to be registered to one another. It should be understood that the following discussion provides one exemplary embodiment of this registration, and is not intended to limit the applicability or characteristics of the invention in any manner.

A computer 16 coupled to the one or more imaging devices 12 controls the operation of imaging devices 12 via target analysis code 18. For example, the computer 16 may be configured to control the orientation and position of the one or more imaging devices 12 to cover the span of interest, control the acquisition of multiple images over the span of interest, process acquired images to create the second model of the object 14, analyze the second model to obtain measurements of the object 14, and so forth.

In the illustrated embodiment, the target analysis code 18 includes image acquisition code 20, target modeling code 22, registration code 24, and image based target analysis code 26. The image acquisition code 20 is adapted to acquire two-dimensional images of various views of the object 14 from the imaging devices 12, such that the acquired images cumulatively cover a desired span of interest of the object 14. The target modeling code 22 is adapted to input, process, create, and/or output a model of the object 14, which is used or processed in conjunction with the acquired images. The registration code 24 is adapted to perform registration of a first model (e.g., theoretical or design model) of the object 14 and each of the acquired images with one another. Thus, the registration code 24 functions to match positions and geometries of the acquired images, using geometrical transformations if needed, with the first model of the object 14. In addition, the target modeling code 22 may be configured to regenerate or create a second model of the object 14 using the multiple images and the first model registered with one another. Thus, the second model may be a modified version of the first model based on the acquired images. In other words, the first model is a theoretical or design model, which is modified according to the real data associated with the images acquired for the object 14 to generate the second model. For example, in certain embodiments, the first model is modified by scaling, rotating and translating the first model based on the real data associated with the images. Once the theoretical model and the real data associated with the images are aligned, the second or the actual model can be reconstructed, measured, and compared against the theoretical model. The model based target analysis code 26 is adapted to analyze characteristics of the object 14 based on the reconstructed second model of the object 14. In certain embodiments, the first model of the object 14 may be a computer aided design (CAD) model of the object 14. Further, in certain embodiments, the first and the second model of the object may be a three-dimensional model of the object 14 and the multiple images acquired by the imaging devices 12 may be a two-dimensional image of the object 14.

As will be appreciated by those skilled in the art, the target analysis code 18 may be embodied in the form of computer program code containing instructions embodied in tangible media, such as floppy diskettes, compact discs, digital video discs, hard drives, or any other computer-readable storage medium. The computer 16 may be any general purpose or special purpose computer adapted to execute the instructions of the target analysis code 18.

In addition, the measurement system 10 may be configured to receive commands and scanning parameters from an operator via the computer 16. For example, the computer 16 may be equipped with a keyboard and/or other input devices 28 by which an operator may control the measurement system 10. Additionally, a display 30 may be coupled to the computer 16 and may be utilized to visualize and/or analyze the object 14. Thus, the operator may visualize and/or analyze the object 14 under inspection, initiate acquisition, interact with the target analysis code 18, and so forth. It should be further noted that the computer 16 may be coupled to other input and output devices, such as printers, plotters, scanners, digitizer pads, digitizer pens, touch screens, networks (e.g., Internet), and so forth. Furthermore, one or more additional computers may be further linked to the measurement system 10, so that more than one operator may perform measurement and/or analysis.

Figure 2:
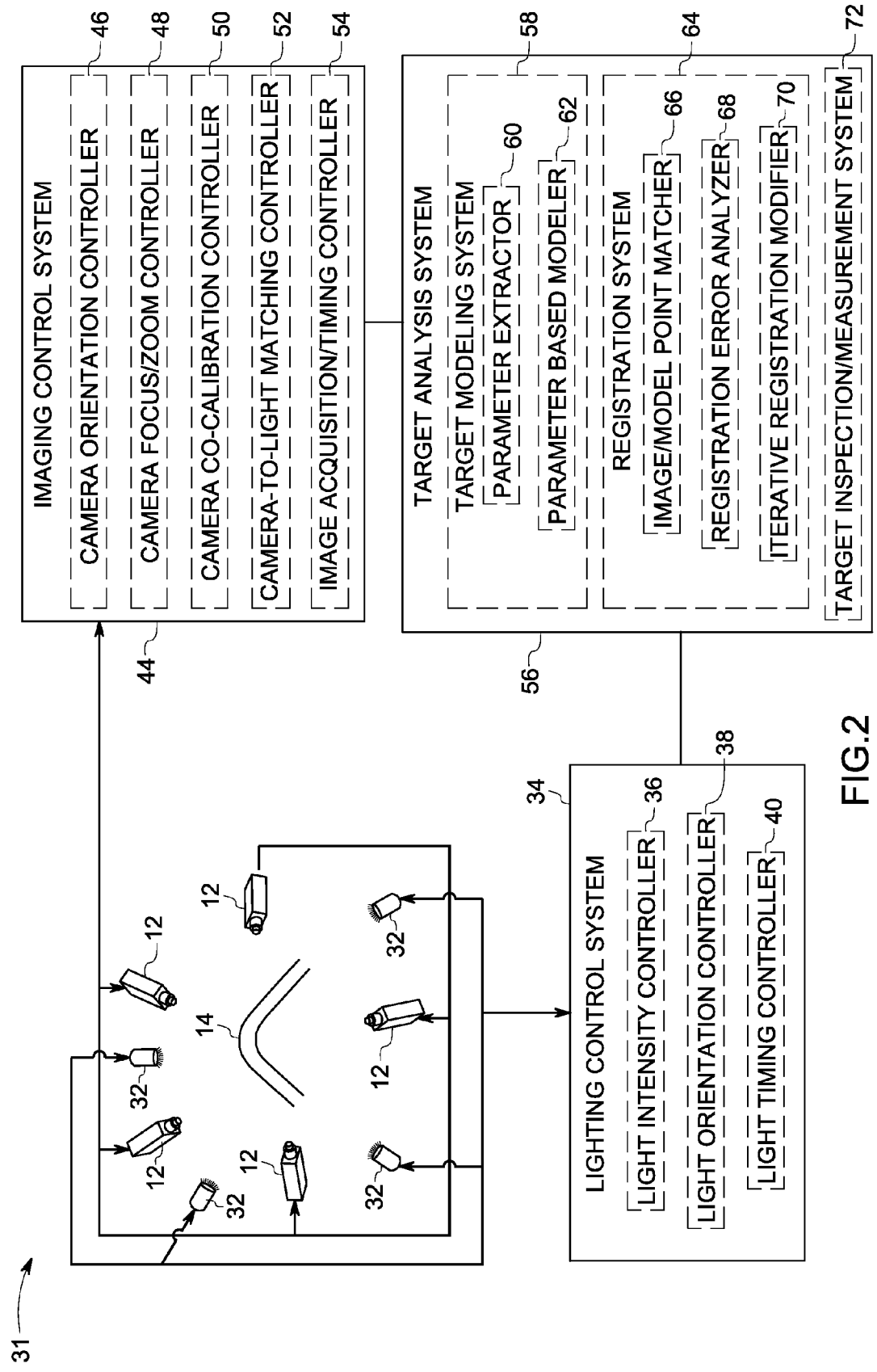
FIG. 2 is a diagrammatical illustration of an exemplary system having an imaging control system coupled to multiple imaging devices, a lighting control system coupled to multiple lighting devices, and a target analysis system using multiple image views and a target model registered with one another in accordance with certain embodiments of the present technique.

Turning now to FIG. 2, this figure illustrates another measurement system 31 in accordance with embodiments of the present technique. As illustrated, the measurement system 31 includes the imaging devices 12 and one or more lighting devices 32, such as backlights, or spot lights or flood lights, which are positioned and oriented to enable the imaging devices 12 to acquire images of silhouettes of the object 14. The operation of one or more lighting devices 32 may be controlled via a lighting control system 34 coupled to the one or more lighting devices 32. The lighting control system 34 may include a light intensity controller 36 for regulating the intensity of light from the lighting devices 32, a light orientation controller 38 for controlling the orientation of lighting devices 32, and a light timing controller 40 for synchronizing the timing of one or more lighting devices 32 with the respective imaging devices 12.

The measurement system 31 further includes an imaging control system 44 coupled to the one or more imaging devices 12 for controlling the operation of imaging devices 12. The imaging control system 44 may include a camera orientation controller 46 for controlling the orientation and/or position of the one or more imaging devices 12, a camera focus/zoom controller 48 for controlling the focus and/or zoom of the imaging devices 12 relative to the object 14, a camera co-calibration controller 50 for calibrating all the imaging devices 12 with respect to each other. In certain embodiments, all imaging devices 12 are co-calibrated so that any three-dimensional point in the field of view of each imaging device can be projected into their respective images. Additionally, calibration of a multi-camera network needs to be performed to map two-dimensional coordinates of the images captured by each imaging device 12 to the three-dimensional volume being viewed by the imaging devices 12. The imaging control system 44 may also include a camera-to-light matching controller 52 for adjusting the operation of imaging devices 12 with the lighting devices 32. The imaging control system 44 may further include an image acquisition/timing controller 54 for initializing the acquisition of two-dimensional images of the object 14 or controlling the timing of operation of the one or more imaging devices 12 while acquiring the two-dimensional images of the object 14.

Further, the lighting control system 34 and the imaging control system 44 may be coupled to a target analysis system 56. The target analysis system 56 performs measurement and/or analysis of the object 14 based on multiple two-dimensional image views and a target model registered to one another. Again, this registration may involve registering the target model to the multiple two-dimensional image views, or vice versa. In one embodiment, the target model may be a three-dimensional CAD model of the object. The target analysis system 56 includes a target modeling system 58 for generating a three-dimensional model of the object 14, which is used or processed in cooperation with the acquired images. The target modeling system further includes a parameter extractor 60 for extracting one or more parameters from the target model, such as the design/theoretical CAD model of the object 14, based on which the three-dimensional model of the object is reconstructed via a parameter-based modeler 62.

The target analysis system 56 also includes a registration system 64 for performing registration of each of the two-dimensional images and the target model with one another. The registration system 64 further includes an image-to-model point matcher 66 for establishing point correspondence among the two-dimensional images based on the target model. A registration error is then computed via a registration error analyzer 68 and the registration is iteratively modified via an iterative registration modifier 70 until the registration error is minimized. A three-dimensional model of the object 14 may be then reconstructed via the target modeling system 58 based on the two-dimensional images and the target model registered with one another. As described above the three-dimensional model of the object 14 is reconstructed by the parameter-based modeler 62 based on a plurality of parameters extracted from the two-dimensional images and the first three-dimensional model of the object 14 via the parameter extractor 60. More specifically, after the plurality of images and the first three-dimensional model of the object 14 have been registered with one another, the model centerline points and radii are reconstructed. Once the three-dimensional model of the object 14 is reconstructed, measurement and/or analysis of various parts of the object 14 are performed to compare it with design parameters via a target inspection/measurement system 72. The parameters are measured from the reconstructed centerline model in the same manner as the parameters are computed for the theoretical/design model.

Figure 3:
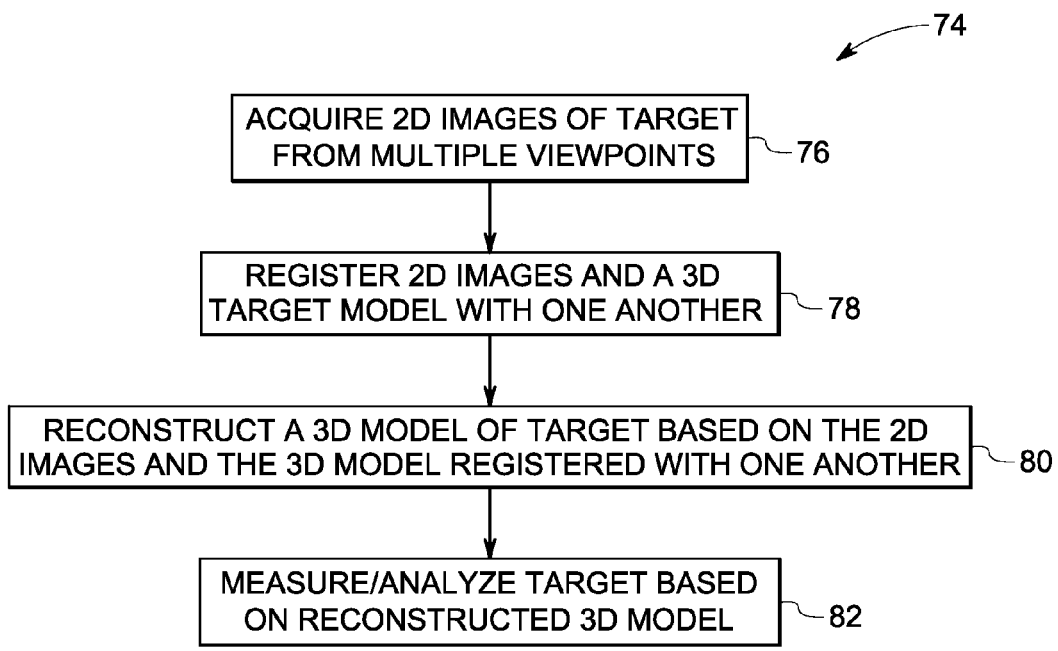
FIG. 3 is a flowchart illustrating a method of measuring and/or analyzing a target based on multiple images and a target model registered with one another in accordance with certain embodiments of the present technique.

FIG. 3 is a flow chart that illustrates an exemplary process 74 for measuring one or more parameters of the object based on model-based measurement techniques using multiple views. Multiple two-dimensional images of the object are acquired from multiple viewpoints via one or more imaging devices at block 76. These viewpoints are optimized to provide a complete coverage of the object (or a desired portion of the object) and thus enable an optimal three-dimensional reconstruction. Each of these two-dimensional images of the object and a three-dimensional target model are then registered at block 78. For example, the target model may be a theoretical or design model of the object in a three-dimensional modeling system, such as a CAD system. The process 74 continues by reconstructing a three-dimensional model of the object based on the multiple two-dimensional images of the object and the three-dimensional target model registered with one another at block 80. Again, this registration may involve registering the target model to the images, registering the images to the target model, or registering the target model and images to another reference or coordinate system. The features in the images, such as edges, are extracted to reconstruct a three-dimensional model of the object. Measurement and/or analysis of various features of the object are then performed at block 82 based on the reconstructed three-dimensional model of the object to report geometrical deviations from the desired dimensions of the respective features.

Figure 4:
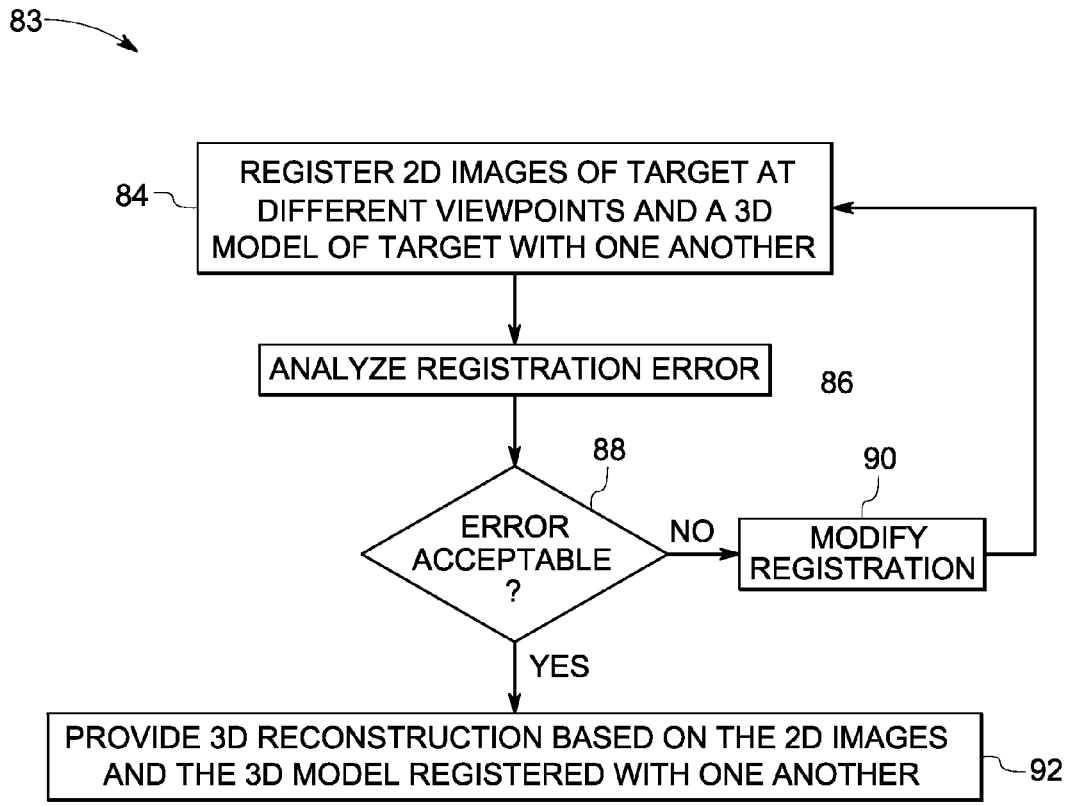
FIG. 4 is a flowchart illustrating a method of reconstructing a model of the object based on multiple images and a target model registered with one another in accordance with certain embodiments of the present technique.

An exemplary registration process 83 is illustrated with reference to FIG. 4. As illustrated, each of the two-dimensional images of the object 14 and the three-dimensional model of the object are registered with one another at block 84. Specifically, the illustrated embodiment involves registering the model to the images, while other embodiments involve registering the images to the model. A registration error is then computed at block 86. Further, the process queries for the acceptable limit on the registration error at block 88. If the error is not acceptable, the error is minimized iteratively until an acceptable limit is reached by modifying registration at block 90. Once the registration error is within the acceptable limit, registration is finalized and a three-dimensional model of the actual object is reconstructed at block 92 based on the two-dimensional images and the three-dimensional model of the object.

For example, in certain embodiments, the registration occurs in multiple steps. Firstly, each of the two-dimensional images of the object and a three-dimensional model of the object are coarsely registered either manually through a user interface or automatically through pre-established transformations. Secondly, a fine registration of the two-dimensional images and the three-dimensional model with one another is performed. For example, the fine registration may be carried out by computing the distance between the profiles or the projections of occluding contours of the model for each viewpoint and the nearest edge in the corresponding image. This distance is computed for several points along the profile of the three-dimensional model, each point corresponding to a sample along the centerline of the model. It should be noted that the occluding contour may be defined as the extreme edge of the object that occludes anything behind it. Thus, occluding contour points, when projected from the edge of the tube, form the outline of the silhouette. Based on geometry of the object, the centerline of the three-dimensional model is sampled at a rate that gives the desired accuracy. For example, the sampling rate may be approximately proportional to the inverse of the local radius of curvature of the model, such that more sample points are needed for a smaller radius of curvature. By further example, two or more sample points may be considered for a straight segment of the model. Occluding contour points are calculated based on the viewpoint of each of the images for all sample points. These occluding contour points are then projected into each two-dimensional image. For a given projected occluding point, a search is conducted along the normal to the projected occluding point for an intensity edge in the image. A registration error is then computed by calculating the distance from the projected occluding point to the edge. This error is summed along the object sample points and across all images. Further, the registration is modified for minimizing the registration error. As the registration error improves, the projected occluding contour points and normals will more closely resemble what is seen in the images and the accuracy of the measurement will improve. Once the error is acceptable or cannot be further improved, registration is finalized and a three-dimensional model of the actual object is reconstructed based on the matched edge points.

Figure 5:
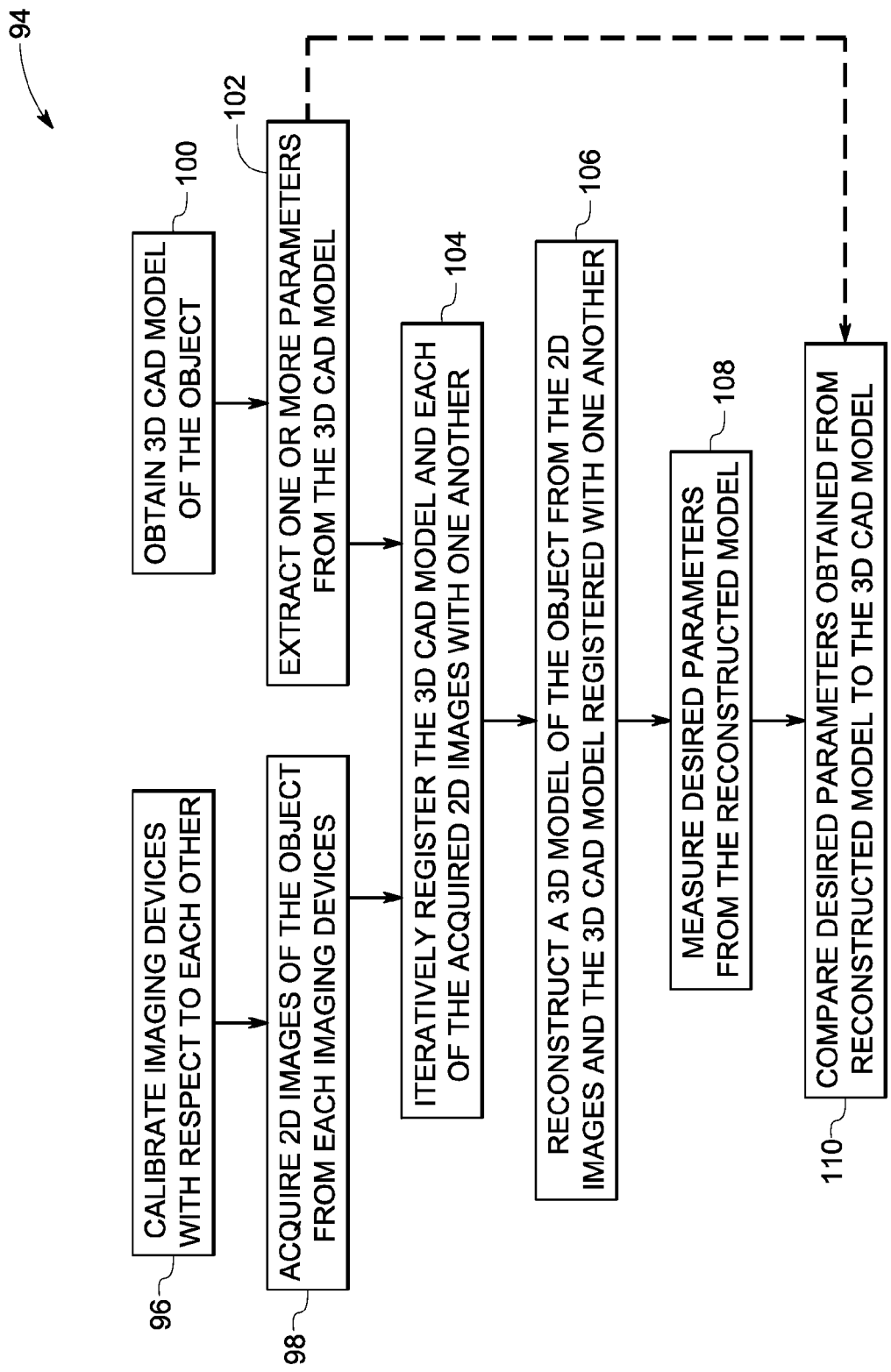
FIG. 5 is a flowchart illustrating a method of measuring a target in accordance with certain embodiments of the present technique.

An exemplary process 94 for measurement of one or more parameters of an object is illustrated via a flowchart depicted in FIG. 5. As illustrated, one or more imaging devices located at various viewpoints are calibrated with respect to each other at block 96. Multiple two-dimensional images of the object are acquired from a plurality of viewpoints via these imaging devices at block 98. A predefined first three-dimension model of the object is obtained at block 100. As described earlier, the first three-dimensional model of the object may be a three-dimensional CAD model of the object defined during the design phase of the object. One or more parameters are extracted from the first three-dimensional model of the object at block 102. For example, these extracted parameters may include a centerline, radius along the centerline, endpoints, intersection points, tangent points, a radius of curvature, a sector angle of the curvature, and so forth. The process 94 further continues by iteratively registering each of the acquired two-dimensional images and the first three-dimensional model of the object with one another at block 104. For example, the process 94 may iteratively register the acquired images and the first model of the object with one another through measurements computed from extracted parameters, i.e., occluding contour points. In this manner, the extracted parameters provide a link or matching criteria for establishing correspondences between different images to provide full coverage of the object. In other words, the process 94 establishes point correspondences between each of the two-dimensional images based on the first three-dimensional model of the object. The process 94 further continues by reconstructing a second three-dimensional model of the object at block 106 from the multiple two-dimensional images and the first three-dimensional model of the object registered with one another. It should be noted that the second three-dimensional model represents characteristics of the actual object, e.g. a manufactured or real object, rather than a theoretical or design of the object. Once the second three-dimensional model representing the actual object is reconstructed, geometrical parameters of the object are calculated from the reconstructed model at block 108. Finally, one or more geometrical parameters are compared with the respective one or more parameters extracted from the first three-dimensional model of the object at block 110 to detect any defect, or deviation from the design parameters, or to direct subsequent manufacturing operations, and so forth.

Figure 6:
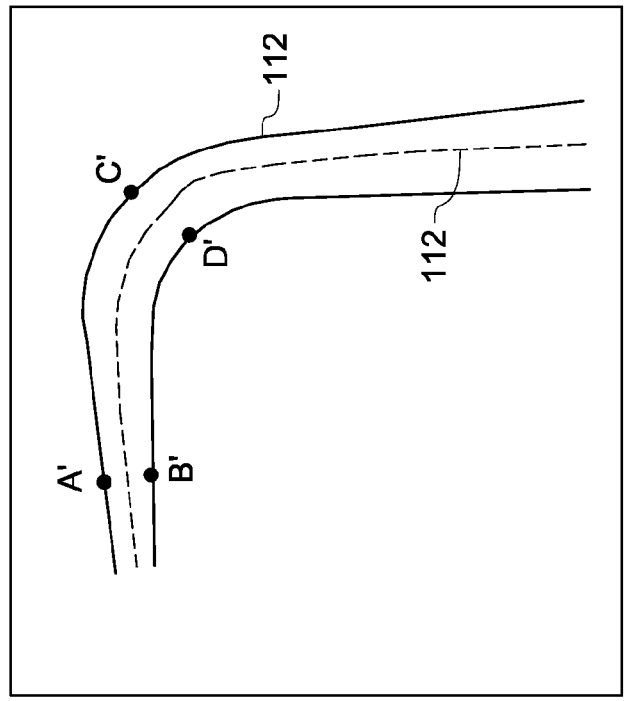
FIG. 6 is a diagrammatical illustration of two-dimensional images acquired by two different imaging devices from two different viewpoints in accordance with certain embodiments of the present technique.
Figure 6:
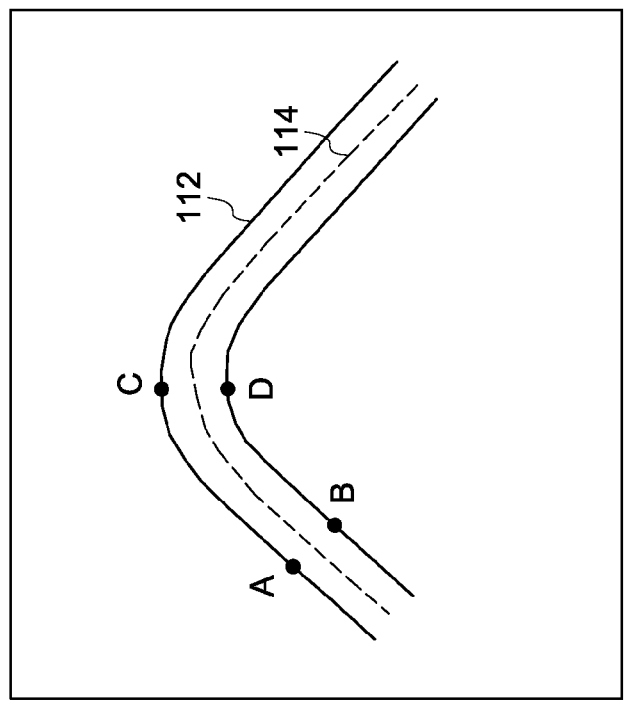

FIG. 6 illustrates an example of model-based measurement of a tube 112 using multiple views in accordance with the techniques described above. As illustrated, image 1 and image 2 correspond to two-dimensional images of the same tube 112 acquired from two different viewpoints. Further, as illustrated in image 1, point A lies along the tube opposite to point B, while point C lies opposite to point D. Additionally, points A, B, C and D in image 1 corresponds to the same points on the tube as point A', B', C' and D' in image 2. Points A, B, C and D lie along the occluding contour of the tube. It should be noted that due to perspective effects, point B does not necessarily lie along the normal of the tube 112 at point A in the illustrated image. Further, based on silhouettes alone, it cannot be concluded with certainty that point B is opposite to point A along the tube 112 or that point A in image 1 corresponds to point A' in image 2. The centerline point corresponding to points A and B is found at the intersection of the normals of the tube 112 at these two points A and B. The target model and the two-dimensional images that are registered with one another are used to identify edge points in each of the images that correspond to the respective centerline points in the model. Given a CAD model for the tube, sample points along the centerline 114 of the tube 112 and a tube radius along the centerline 114 may be extracted. As described earlier, the number of sample points for a curvature may be approximately proportional to the inverse of local radius of curvature of the tube 112. Additionally, a straight segment of the tube 112 may have two or more sample points. Further, for each sample point along the centerline 114, a local normal and tangent to the centerline 114 are extracted. Thus, for a given model of the object and normals, we identify edge points that correspond to a given centerline point, thereby establishing point correspondences across images.

Further, predicted silhouettes comprising projected occluding contours or contour points are coarsely registered to the acquired images using a priori transform or manual initialization. The projected occluding points (A/B, C/D) that correspond to each centerline point are calculated based on the known tube radius and the viewpoints. More specifically, the occluding contour is computed for a known three-dimensional position of the centerline point, and the tangent, the normal, the bi-normal to the centerline point, and the radius at the centerline point. The occluding contour is then projected into each image via a projection matrix of the imaging devices to find the three-dimensional point that should appear in each of the images. Further, an edge, i.e. a linked chain of peaks in the image gradient, is searched for in each image along each of the model normals at each model-point (A, B, C, D). More specifically, the three-dimensional centerline point and a point beyond the occluding contour along the same normal are projected into the image. A two-dimensional line segment is then formed from these two projected points. The edge point is then identified along the two-dimensional line segment by locating a point with maximum gradient. Once an edge is located, it is paired with the corresponding model-point or projected occluding contour. A mean square error for registration is determined based on the distance between model points and edge points. Further, the registration of the three-dimensional model and the two-dimensional images with one another is iteratively refined by adjusting the three-dimensional transformation for the model to minimize the mean square error and hence the registration error, thereby aligning the three-dimensional model with the images. The transformation is parameterized by a matrix of translation, rotation, and scale. This matrix is iteratively adjusted during the registration to minimize the error. Once the registration error is minimized and the registration is finalized, the centerline 114 of the actual tube 112 or samples of it can be calculated in each image by using the occluding edge points from the intensity edges and the local normals at these occluding edge points. The corresponding centerline point can then be calculated and a three-dimensional model of the actual centerline 114 is reconstructed based on the matched edge points (A-A', B-B', and others). Finally, the measurement of one or more features such as tangent points, intersection points and others are extracted from the reconstructed model of the centerline of the tube 112.

The model-based measurement techniques using multiple views described in the various embodiments mentioned above provides measurements of tubes, including curved sections, by utilizing the CAD model to establish point correspondences between images. This eliminates the need to put fiducial marks on the tube to establish point correspondences. The techniques described above are based on registration-driven matching algorithm, by which symmetric points on the surface of the object are determined from known symmetric points on the surface of a model of the object such as CAD model. Once these matches are found, the corresponding parameters of the object at that location are determined by a triangulation/reconstruction across multiple views. Further, as will be appreciated by one skilled in the art, the techniques described in the various embodiments discussed above enable measurement of an object using a computer and one or more imaging devices. The technique therefore is inexpensive, programmable and flexible, enabling more accurate measurements of several types of objects (e.g., different tube models) with a single system. The techniques may help in identification of deformities or defects in the alignment, size, or structure of the object. Further, it will be appreciated by one skilled in the art that the techniques may be employed for or may be modified to suit various applications including inspection of complex parts such as tubular or curved surfaces of any object and others.

As will be also appreciated, the above described techniques may take the form of computer or controller implemented processes and apparatuses for practicing those processes. The disclosure can also be embodied in the form of computer program code containing instructions embodied in tangible media, such as floppy diskettes, compact discs, digital video discs, hard drives, or any other computer-readable storage medium, wherein the computer program code is loaded into and executed by a computer or controller.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of measuring an object, the method comprising:
   registering each of a plurality of images of an object and a first model of the object with one another, wherein the plurality of images comprise different views of the object, wherein registering comprises sampling the object based on a geometry of the object, and further wherein sampling comprises a sampling rate proportional to the inverse of a local radius of curvature of at least a part of the object; and
   reconstructing a second model of the object based on the plurality of images and the first model registered with one another.

2. The method of claim 1, comprising obtaining the plurality of images at the different views for cumulatively covering a desired area of the object.

3. The method of claim 1, comprising obtaining the plurality of images from a plurality of imaging devices.

4. The method of claim 3, comprising co-calibrating the plurality of imaging devices to map a coordinate of each of the plurality of images to a reference coordinate system.

5. The method of claim 1, comprising arranging lighting relative to the object to provide a silhouette of the object in each of the plurality of images.

6. The method of claim 1, wherein registering comprises computing a plurality of occluding contour points for each of the plurality of images of the object.

7. The method of claim 1, wherein registering comprises establishing point correspondences between each of the plurality of images through the first model of the object.

8. The method of claim 1, wherein sampling comprises at least two sample points on a straight segment of at least a part of the object.

9. The method of claim 1, further comprising iterating the step of registering for minimizing a registration error.

10. The method of claim 1, wherein reconstructing the second model comprises reconstructing a model of the object based on one or more edge points matched between the plurality of images, wherein the one or more edge points are derived from the plurality of images and the first model registered with one another.

11. The method of claim 1, comprising measuring one or more features of the object from the second model.

12. The method of claim 11, wherein measuring the one or more features comprise measuring tangent points, or intersection points, or combinations thereof.

13. The method of claim 1, wherein each of the plurality of images is a two-dimensional image of the object and wherein the first and the second model is a three-dimensional model of the object.

14. A measurement system comprising:
    a plurality of imaging devices for acquiring a plurality of images of at least a part of the object from a plurality of viewpoints; and
    a modeling system coupled to the plurality of imaging devices, wherein the modeling system is configured to sample the object based on a geometry of the object configured to register each of the plurality of images and a first model of the object with one another, and configured to reconstruct a second model of the object based on the plurality of images and the first model registered with one another, wherein a rate of sampling the object is proportional to the inverse of a local radius of curvature of at least a part of the object.

15. The system of claim 14, further comprising a plurality of lighting devices for enabling the plurality of imaging devices to acquire a silhouette of the object in each of the plurality of images.

16. The system of claim 14, wherein the modeling system is further configured to measure one or more features of the object based on the second model.

17. The system of claim 14, wherein each of the plurality of images is a two-dimensional image of the object and wherein the first and the second model is a three-dimensional model of the object.

18. A computer readable media, comprising:
    code adapted to register each of a plurality of images of an object and a first model of the object with one another, wherein the images comprise different views of the object, wherein code adapted to register comprises code adapted to sample the object based on a geometry of the object, and further wherein sampling comprises a sampling rate proportional to the inverse of a local radius of curvature of at least a part of the object; and
    code adapted to reconstruct a second model of the object based on the plurality of images and the first model registered with one another.

19. The computer readable media of claim 18, further comprising code adapted to iterate the step of registering for minimizing a registration error.

20. The computer readable media of claim 18, further comprising code adapted to measure one or more features of the object from the second model.

* * * * *